(12) United States Patent
Skurkis et al.

(10) Patent No.: US 8,997,563 B2
(45) Date of Patent: Apr. 7, 2015

(54) VEHICLE SENSOR SYSTEM (71) Applicant: GM Global Technology Operations LLC, Detroit, MI (US)

(72) Inventors: Richard J. Skurkis, Lake Orion, MI (US); Guillermo A. Herrera, Winnetka, CA (US); Nancy L. Johnson, Northville, MI (US); Alan L. Browne, Grosse Pointe, MI (US); Nicholas W. Pinto, IV, Ferndale, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 260 days.

(21) Appl. No.: 13/750,441

(22) Filed: Jan. 25, 2013

(65) Prior Publication Data
US 2014/0211826 A1 Jul. 31, 2014

(51) Int. Cl.
*G08B 19/02* (2006.01)
*G01N 27/04* (2006.01)
(52) U.S. Cl.
CPC ................................. *G01N 27/041* (2013.01)
(58) Field of Classification Search
CPC ....... B64D 15/163; B64D 15/20; G08D 19/02

USPC ...................... 73/432.1; 374/46, 51; 340/580; 244/134 A–134 F
See application file for complete search history.

(56) References Cited

U.S. PATENT DOCUMENTS

| 2,803,813 | A | * | 8/1957 | Bullen et al. | 340/580 |
| 4,873,510 | A | * | 10/1989 | Khurgin | 340/580 |
| 2005/0238503 | A1 | * | 10/2005 | Rush et al. | 417/322 |

* cited by examiner

*Primary Examiner* — Eric S McCall
*Assistant Examiner* — Anthony W Megna Fuentes
(74) *Attorney, Agent, or Firm* — Quinn Law Group, PLLC (57) ABSTRACT

A sensor system includes a housing defining a cavity, an actuator formed from an alloy transitionable between first and second states, a plunger attached to the actuator, and a resilient member configured for translating the plunger within the cavity. The plunger is not translatable during a first condition in which a coating of debris is disposed on the housing as the alloy transitions between the first and second states to define a first stress on the actuator. The plunger is translatable during a second condition in which the housing is substantially free from the coating as the alloy transitions to define a second stress on the actuator that is less than the first stress. The alloy transitions from the first to the second state at a first transformation temperature during the first condition, and at a second transformation temperature that is less than the first temperature during the second condition.

19 Claims, 6 Drawing Sheets

VEHICLE SENSOR SYSTEM

TECHNICAL FIELD

The present disclosure relates to a sensor system for a vehicle.

BACKGROUND

Debris, such as ice or mud, may build up on vehicle components and surfaces during vehicle operation. For example, during inclement and/or dirty operating conditions, ice or mud may coat windshield wipers, power mirrors, back-up sensors, aircraft wings, control surfaces, and the like.

SUMMARY

A sensor system for a vehicle includes a housing defining a cavity therein, and an actuator attached to the housing within the cavity. The actuator is formed from a shape memory alloy transitionable in response to a thermal activation signal between a first temperature-dependent state and a second temperature-dependent state. The sensor system also includes a plunger attached to the actuator and translatable within the cavity. The plunger is not translatable within the cavity during a first condition in which a coating of debris is disposed on the housing as the shape memory alloy transitions between the first-temperature dependent state and the second temperature-dependent state to thereby define a first stress on the actuator. The plunger is translatable within the cavity during a second condition in which the housing is substantially free from the coating of debris as the shape memory alloy transitions between the first temperature-dependent state and the second temperature-dependent state to thereby define a second stress on the actuator that is less than the first stress. The shape memory alloy transitions from the first temperature-dependent state to the second temperature-dependent state at a first transformation temperature during the first condition. The shape memory alloy transitions from the first temperature-dependent state to the second temperature-dependent state at a second transformation temperature that is less than the first transformation temperature during the second condition. The sensor system also includes a resilient member configured for translating the plunger within the cavity after the shape memory alloy transitions from the second temperature-dependent state to the first temperature-dependent state.

In one embodiment, the housing has a proximal end and a distal end spaced apart from the proximal end. The sensor system also includes a flexible membrane disposed on the proximal end. The sensor system further includes the actuator attached to the housing within the cavity at the distal end. In addition, the sensor system includes the plunger attached to the actuator. The plunger is translatable within the cavity and abuttable with the flexible membrane. The sensor system also includes a resilient member configured for translating the plunger within the cavity after the shape memory alloy transitions from the second temperature-dependent state to the first temperature-dependent state. The resilient member retracts the plunger into the cavity towards the distal end after the shape memory alloy transitions from the second temperature-dependent state to the first temperature-dependent state so that the plunger does not abut the flexible membrane, and the flexible membrane does not protrude from the housing at the proximal end. The actuator translates the plunger within the cavity towards the proximal end during the first condition as the shape memory alloy transitions from the first temperature-dependent state to the second temperature-dependent state so that the plunger abuts the flexible membrane, and the flexible membrane does not protrude from the housing at the proximal end. Further, the actuator translates the plunger within the cavity towards the proximal end during the second condition as the shape memory alloy transitions from the first temperature-dependent state to the second temperature-dependent state so that the plunger abuts the flexible membrane and the flexible membrane protrudes from the housing at the proximal end.

A vehicle includes a body defining an aperture therein, and a sensor system disposed within the aperture. The sensor system includes a housing defining a cavity therein, and an actuator attached to the housing within the cavity. The actuator is formed from a shape memory alloy transitionable in response to a thermal activation signal between a first temperature-dependent state and a second temperature-dependent state. The sensor system also includes a plunger attached to the actuator and translatable within the cavity. The plunger is not translatable within the cavity during a first condition in which a coating of debris is disposed on the housing as the shape memory alloy transitions between the first-temperature dependent state and the second temperature-dependent state to thereby define a first stress on the actuator. The plunger is translatable within the cavity during a second condition in which the housing is substantially free from the coating of debris as the shape memory alloy transitions between the first temperature-dependent state and the second temperature-dependent state to thereby define a second stress on the actuator that is less than the first stress. The shape memory alloy transitions from the first temperature-dependent state to the second temperature-dependent state at a first transformation temperature during the first condition. The shape memory alloy transitions from the first temperature-dependent state to the second temperature-dependent state at a second transformation temperature that is less than the first transformation temperature during the second condition. The sensor system also includes a resilient member configured for translating the plunger within the cavity after the shape memory alloy transitions from the second temperature-dependent state to the first temperature-dependent state.

The above features and advantages and other features and advantages of the present invention will be readily apparent from the following detailed description of the preferred embodiments and best modes for carrying out the present invention when taken in connection with the accompanying drawings and appended claims.

DETAILED DESCRIPTION

Figure 1:
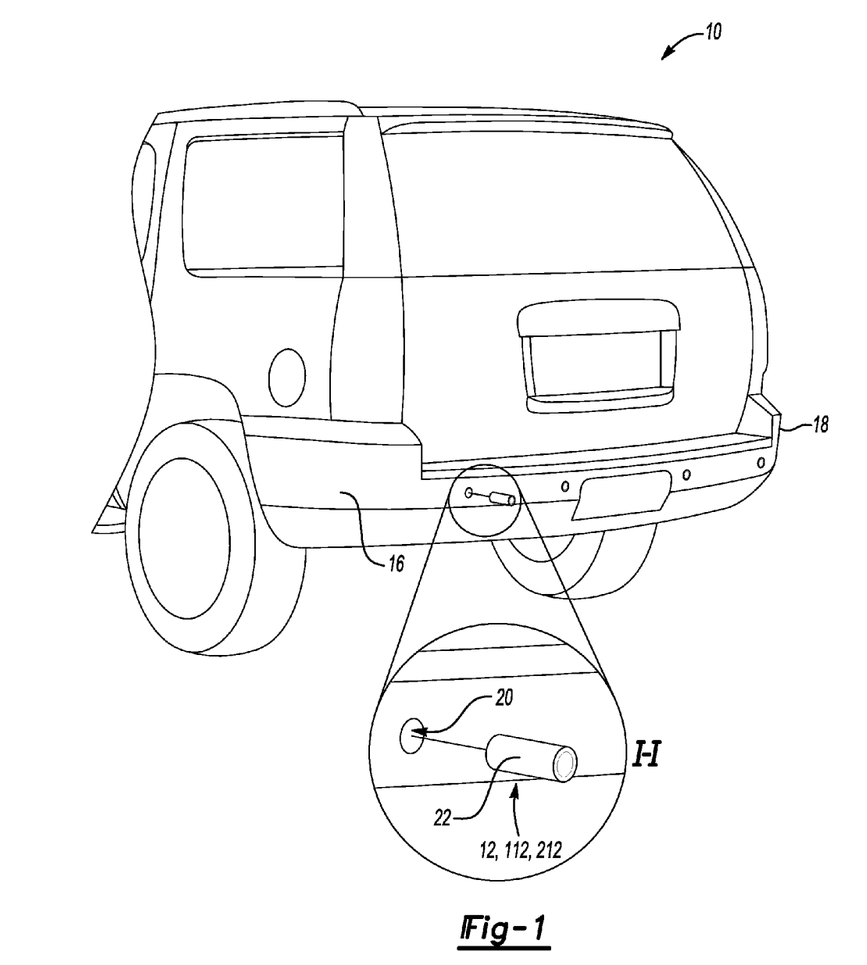
FIG. 1 is a schematic perspective illustration of a portion of a vehicle and includes an exploded and magnified view of a sensor system of the vehicle at I-I.

Referring to the Figures, wherein like reference numerals refer to like elements, a vehicle 10 including a sensor system 12, 112, 212 is shown in FIG. 1. The sensor system 12, 112, 212 may be useful for vehicles 10, such as automobiles and aircraft, that require detection of a coating of debris (shown generally at 14 in FIGS. 2A and 2B) on a surface 16 of the vehicle 10. For example, the sensor system 12, 112, 212 may be useful for detecting a coating of ice and/or mud that is disposed on a vehicle component or surface 16. More specifically, the coating of debris 14 may be any substance impeding a line of sight of the sensor system 12, 112, 212, such as, but not limited to, water, ice, fog, dirt, dust, salt, particles, smudges, objects, and combinations thereof. As such, the sensor system 12, 112, 212 may protect vehicle components such as power mirrors, wipers, windows, sensors, such as back-up sensors, and the like, and vehicle surfaces 16 such as control surfaces and/or aircraft wings. Therefore, the sensor system 12, 112, 212 may be useful for icy, dusty, dirty, and/or wet operating environments, and may also be useful for non-vehicular applications including, for example, security or monitoring applications.

With continued reference to FIG. 1, the vehicle 10 includes a body 18 defining an aperture 20 therein, and the sensor system 12, 112, 212 is disposed within the aperture 20. For example, the body 18 may be a body panel or component of the vehicle 10, such as a rear liftgate, a side body panel, a front or rear bumper, a side-view mirror, a control surface, a wing, and the like, and the aperture 20 may be configured for receiving the sensor system 12, 112, 212.

Referring now to FIGS. 2A-2D, the sensor system 12 includes a housing 22 defining a cavity 24 therein. The housing 22 may have a proximal end 26 and a distal end 28 spaced apart from the proximal end 26. Further, the housing 22 may have a central longitudinal axis 30 extending from the proximal end 26 to the distal end 28 along which a plunger 40 may translate within the cavity 24, as set forth in more detail below.

With continued reference to FIGS. 2A-2D, the sensor system 12 further includes an actuator 32 attached to the housing 22 within the cavity 24. The actuator 32 is formed from a shape memory alloy transitionable in response to a thermal activation signal (shown generally at 34 in FIGS. 2B and 2D), e.g., heat, between a first temperature-dependent state (shown generally at 36 in FIGS. 2A and 2C) and a second temperature-dependent state (shown generally at 38 in FIGS. 2B and 2D). In particular, the actuator 32 may be attached to the distal end 28 of the housing 22. Therefore, as set forth in more detail below, the actuator 32 may actuate the plunger 40 by transitioning between the first temperature-dependent state 36 and the second temperature-dependent state 38 such that the plunger 40 translates within the cavity 24.

As used herein, the terminology "shape memory alloy" refers to alloys that exhibit a shape memory effect and have the capability to quickly change properties in terms of stiffness, spring rate, and/or form stability. That is, the shape memory alloy may undergo a solid state crystallographic phase change via molecular or crystalline rearrangement to shift between a martensite phase, i.e., "martensite", and an austenite phase, i.e., "austenite". Stated differently, the shape memory alloy may undergo a displacive transformation rather than a diffusional transformation to shift between martensite and austenite. A displacive transformation is defined as a structural change that occurs by the coordinated movement of atoms or groups of atoms relative to neighboring atoms or groups of atoms. In general, the martensite phase refers to the comparatively lower-temperature phase and is often more deformable than the comparatively higher-temperature austenite phase.

The temperature at which the shape memory alloy begins to change from the austenite phase to the martensite phase is known as the martensite start temperature, $M_s$. The temperature at which the shape memory alloy completes the change from the austenite phase to the martensite phase is known as the martensite finish temperature, $M_f$. Similarly, as the shape memory alloy is heated, the temperature at which the shape memory alloy begins to change from the martensite phase to the austenite phase is known as the austenite start temperature, $A_s$. The temperature at which the shape memory alloy completes the change from the martensite phase to the austenite phase is known as the austenite finish temperature, $A_f$.

The shape memory alloy may have any suitable form, i.e., shape. For example, the actuator 32 may be configured as a shape-changing element such as a wire 126 (FIG. 6), spring (shown generally in FIGS. 4A-4D), tape, band, continuous loop, and combinations thereof. Further, the shape memory alloy may have any suitable composition. In particular, the shape memory alloy may include in combination an element selected from the group of cobalt, nickel, titanium, indium, manganese, iron, palladium, zinc, copper, silver, gold, cadmium, tin, silicon, platinum, and gallium. For example, suitable shape memory alloys may include nickel-titanium based alloys, nickel-aluminum based alloys, nickel-gallium based alloys, indium-titanium based alloys, indium-cadmium based alloys, nickel-cobalt-aluminum based alloys, nickel-manganese-gallium based alloys, copper based alloys (e.g., copper-zinc alloys, copper-aluminum alloys, copper-gold alloys, and copper-tin alloys), gold-cadmium based alloys, silver-cadmium based alloys, manganese-copper based alloys, iron-platinum based alloys, iron-palladium based alloys, and combinations of one or more of each of these combinations. The shape memory alloy can be binary, ternary, or any higher order so long as the shape memory alloy exhibits a shape memory effect, e.g., a change in shape orientation, damping capacity, and the like. Generally, the shape memory alloy may be selected according to desired operating temperatures of the sensor system 12, 112, 212. In one specific example, the shape memory alloy may include nickel and titanium.

Therefore, the actuator 32 formed from the shape memory alloy may be characterized by a cold state, i.e., when a temperature of the shape memory alloy is below the martensite finish temperature, $M_f$, of the shape memory alloy. Likewise, the actuator 32 formed from the shape memory alloy may also be characterized by a hot state, i.e., when the temperature of the shape memory alloy is above the austenite finish temperature, $A_f$, of the shape memory alloy. In addition, although not shown, the sensor system 12, 112, 212 may include a plurality of actuators 32 formed from the shape memory alloy.

Referring again to FIGS. 2A-2D, the sensor system 12 also includes the plunger 40 attached to the actuator 32 and translatable within the cavity 24. More specifically, the plunger 40 may translate within the cavity 24 along the central longitudinal axis 30 and may be actuated by the actuator 32, as set forth in more detail below. The plunger 40 may have an attachment end 42 attached to the actuator 32 and spaced apart from the proximal end 26, and an indicator end 44 spaced apart from the attachment end 42. Further, as shown in FIGS. 2A-2D, the proximal end 26 of the housing 22 may be spaced apart from the actuator 32, and the plunger 40 may protrude from the cavity 24 at the proximal end 26.

As described with reference to FIGS. 2A and 2B, the plunger 40 may not be translatable within the cavity 24 during a first condition (shown generally at 48) in which the coating of debris 14 is disposed on the housing 22 as the shape memory alloy transitions between the first temperature-dependent state 36 (FIG. 2A) and the second temperature-dependent state 38 (FIG. 2B) to thereby define a first stress (indicated generally at 46 in FIG. 2B) on the actuator 32. That is, the housing 22 and/or protruding portion of the plunger 40 may be substantially coated, covered, caked, or obstructed with the coating of debris 14 during the first condition 48. Stated differently, during the first condition 48, the housing 22 is not free from the coating of debris 14, but is rather at least partially covered with the coating of debris 14.

Figure 2A:
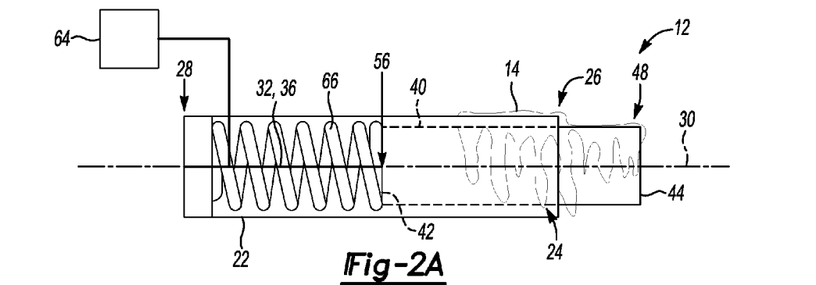
FIG. 2A is a schematic illustration of a side view of one embodiment of the sensor system of FIG. 1 during a first condition, wherein a coating of debris is disposed on the sensor system, before actuation of an actuator formed from a shape memory alloy.
Figure 2B:
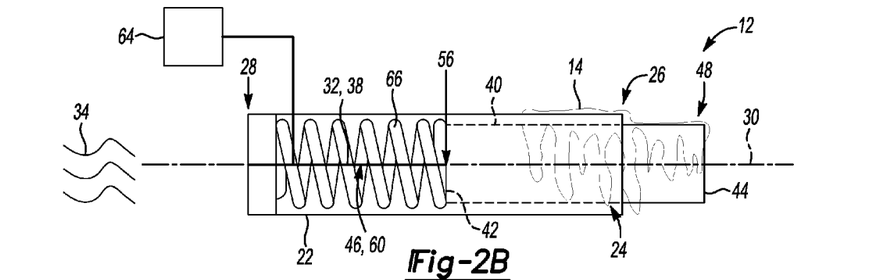
FIG. 2B is a schematic illustration of a side view of the sensor system of FIG. 2A during the first condition after actuation of the actuator.
Figure 2C:
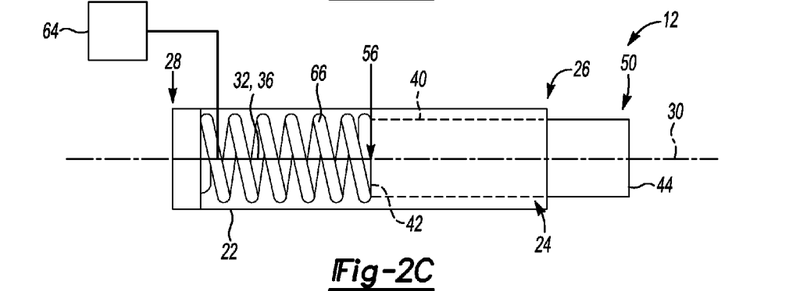
FIG. 2C is a schematic illustration of a side view of the sensor system of FIG. 2A during a second condition, wherein the sensor system is substantially free from the coating of debris, before actuation of the actuator.
Figure 2D:
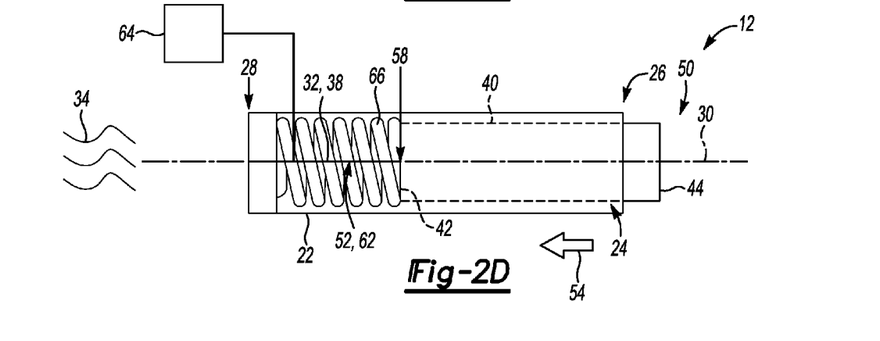
FIG. 2D is a schematic illustration of a side view of the sensor system of FIG. 2C during the second condition after actuation of the actuator.

Likewise, referring to FIGS. 2C and 2D, the plunger 40 is translatable within the cavity 24 during a second condition (shown generally at 50) in which the housing 22 is substantially free from the coating of debris 14 (FIGS. 2A and 2B) as the shape memory alloy transitions between the first temperature-dependent state 36 (FIG. 2C) and the second temperature-dependent state 38 (FIG. 2D) to thereby define a second stress (indicated generally at 52 in FIG. 2D) on the actuator 32 that is less than the first stress 46 (FIG. 2B). As used herein, the terminology "substantially free from the coating of debris 14" refers to a circumstance wherein the housing 22 is not coated, covered, caked, or obstructed with the coating of debris 14 so that the plunger 40 may translate along the central longitudinal axis 30.

More specifically, with continued reference to FIG. 2D, the actuator 32 may retract the plunger 40 into the cavity 24 in the direction of arrow 54 during the second condition 50 as the shape memory alloy transitions from the first temperature-dependent state 36 (FIG. 2C) to the second temperature-dependent state 38 (FIG. 2D). That is, as the shape memory alloy transitions from the first temperature-dependent state 36 to the second temperature-dependent state 38 in response to the thermal activation signal 34 (FIG. 2D), the shape memory alloy may contract and pull the plunger 40 into the cavity 24 in the direction of arrow 54.

In particular, referring again to FIGS. 2C and 2D, during the second condition 50, the plunger 40 may be unencumbered by the coating of debris 14 (FIGS. 2A and 2B) and may freely translate into the cavity 24 upon actuation of the shape memory alloy, i.e., upon transition of the shape memory alloy from the first temperature-dependent state 36 (FIG. 2C) to the second temperature-dependent state 38 (FIG. 2D). For example, during the second condition 50, the attachment end 42 of the plunger 40 may translate along the central longitudinal axis 30 from a first position 56 (FIG. 2C) on the central longitudinal axis 30 to a second position 58 (FIG. 2D) on the central longitudinal axis 30.

However, in contrast, during the first condition 48 as shown in FIGS. 2A and 2B, the attachment end 42 may not translate from the first position 56 on the central longitudinal axis 30. That is, during the first condition 48, the plunger 40 may be encumbered by the coating of debris 14 disposed on the housing 22, and may not translate freely within the cavity 24.

The shape memory alloy transitions from the first temperature-dependent state 36 (FIG. 2A) to the second temperature-dependent state 28 (FIG. 2B) at a first transformation temperature, during the first condition 48 (FIGS. 2A and 2B). However, during the second condition 50 (FIGS. 2C and 2D), the shape memory alloy transitions from the first temperature-dependent state 36 (FIG. 2C) to the second temperature-dependent state 38 (FIG. 2D) at a second transformation temperature, $T_{trans2}$, that is less than the first transformation temperature, $T_{trans1}$. That is, the actuator 32 formed from the shape memory alloy is actuatable at a lower transformation temperature, $T_{trans2}$, during the second condition 50 than during the first condition 48.

Therefore, referring again to FIGS. 2A and 2B, during the first condition 48, as the shape memory alloy transitions from the first temperature-dependent state 36 (FIG. 2A) to the second temperature-dependent state 38 (FIG. 2B) at the first transformation temperature, $T_{trans1}$, the plunger 40 is not translatable within the cavity 24 since the coating of debris 14 encumbers the plunger 40 and minimizes translation of the plunger 40 within the cavity 24.

During the first condition 48, as the shape memory alloy transitions from the first temperature-dependent state 36 to the second temperature-dependent state 38, the actuator 32 may attempt to contract in length, i.e., shorten, and may unsuccessfully attempt to translate the plunger 40 towards the distal end 28 within the cavity 24 due to the resistance provided by the coating of debris 14 disposed on the housing 22. Such lack of translation of the plunger 40 may define the first stress 46 (FIG. 2B) on the actuator 32. That is, during the first condition 48 in which the housing 22 is substantially covered with the coating of debris 14, the first stress 46 is defined on the actuator 32 as the actuator 32 attempts to translate the plunger 40 from the first position 56 (FIG. 2A).

However, referring to FIGS. 2C and 2D, during the second condition 50 in which the housing 22 is not substantially covered with the coating of debris 14 (FIGS. 2A and 2B), the plunger 40 is translatable within the cavity 24. That is, as the shape memory alloy transitions from the first temperature-dependent state 36 (FIG. 2C) to the second temperature-dependent state 38 (FIG. 2D) at the second transformation temperature, $T_{trans2}$, the plunger 40 is translatable within the cavity 24 since the coating of debris 14 does not encumber the plunger 40, but instead allows translation of the plunger 40 within the cavity 24. During the second condition 50, as the shape memory alloy transitions from the first temperature-dependent state 36 to the second temperature-dependent state 38, the actuator 32 may contract in length, i.e., shorten, and may therefore translate the plunger 40 towards the distal end 28 within the cavity 24. Such translation of the plunger 40 may minimize strain on the actuator 32 and thereby define the second stress 52 on the actuator 32. The second stress 52 is less than the first stress 46 (FIG. 2B) since the plunger 40 may translate freely within the cavity 24 during the second condition 50. That is, during the second condition 50 in which the housing 22 is substantially free from the coating of debris 14, the second stress 52 is defined on the actuator 32 as the actuator 32 translates the plunger 40 from the first position 56 (FIG. 2A).

As such, the first stress 46 may correlate to and indicate the first condition 48. Similarly, the second stress 52 may correlate to and indicate the second condition 50. Therefore, the sensor system 12 may be configured to detect the first condition 48 wherein the coating of debris 14 is disposed on the housing 22 and/or plunger 40.

Furthermore, the shape memory alloy may exhibit a first electrical resistance 60 (FIG. 2B) during the first condition 48 (FIG. 2B) upon actuation of the actuator 32, and may exhibit a second electrical resistance 62 (FIG. 2D) during the second condition 50 (FIG. 2D) upon actuation of the actuator 32 that is less than the first electrical resistance 60. Therefore, the first electrical resistance 60 may correlate to and indicate the first condition 48. Similarly, the second electrical resistance 62 may correlate to and indicate the second condition 50.

As such, referring to FIG. 2B, the sensor system 12 may further include a controller 64 connected to the actuator 32 and configured for indicating the first electrical resistance 60 and/or the first stress 46. The controller 64 and sensor system 12 may be configured to detect the first condition 48 wherein the housing 22 and/or plunger 40 is substantially covered with the coating of debris 14, e.g., ice and/or mud.

In addition, referring again to FIGS. 2C and 2D, the sensor system 12 further includes a resilient member 66 configured for translating the plunger 40 within the cavity 24 after the shape memory alloy transitions from the second temperature-dependent state 38 (FIG. 2D) to the first temperature-dependent state 36 (FIG. 2C). For example, the resilient member 66 may translate the plunger 40 from the second position 58 (FIG. 2D) to the first position 56 (FIG. 2C) so that the plunger 40 protrudes from the housing 22 at the proximal end 26 as the shape memory alloy transitions from the second temperature-dependent state 38 to the first temperature-dependent state 36. In one non-limiting example, the resilient member 66 may be a spring and may bias the plunger 40 to the first position 56. Stated differently, the resilient member 66 may reset the sensor system 12 and the plunger 40 as the shape memory alloy transitions from the second temperature-dependent state 38 to the first temperature-dependent state 36.

Figure 3A:
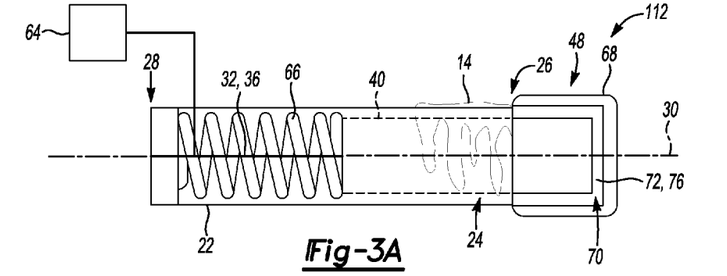
FIG. 3A is a schematic illustration of a side view of another embodiment of the sensor system of FIG. 1 during the first condition before actuation of the actuator formed from the shape memory alloy.
Figure 3B:
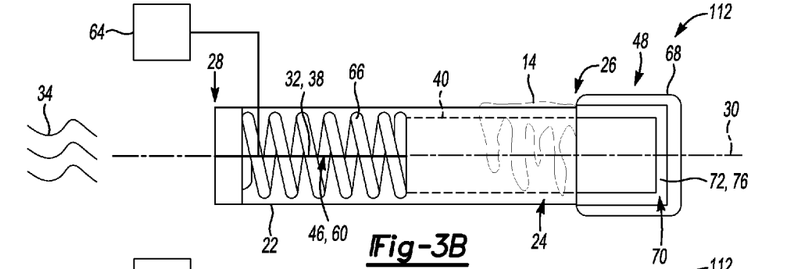
FIG. 3B is a schematic illustration of a side view of the sensor system of FIG. 3A during the first condition after actuation of the actuator.
Figure 3C:
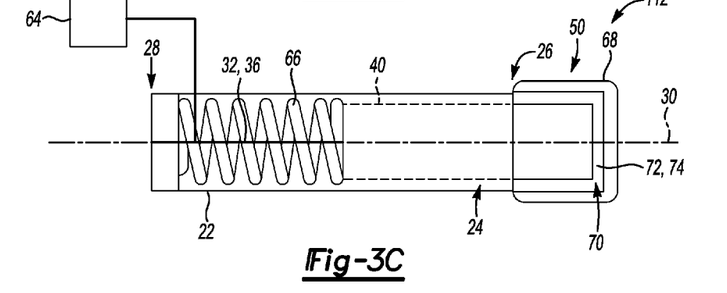
FIG. 3C is a schematic illustration of a side view of the sensor system of FIG. 3A during the second condition before actuation of the actuator.
Figure 3D:
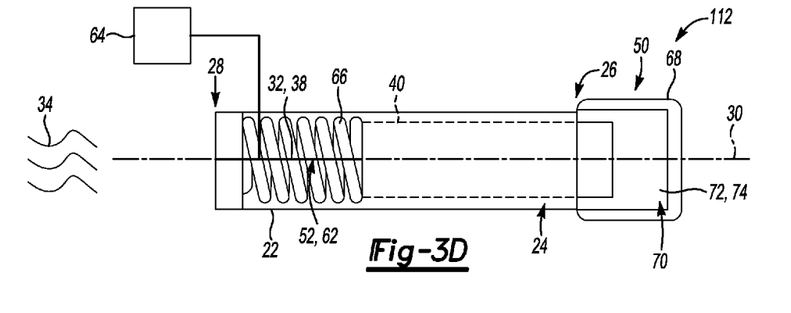
FIG. 3D is a schematic illustration of a side view of the sensor system of FIG. 3C during the second condition after actuation of the actuator.

Referring now to FIGS. 3A-3D, in another embodiment, the sensor system 112 further includes a cap 68 attached to the proximal end 26 and defining a chamber 70 therein. The chamber 70 may be disposed in communication with the cavity 24 so that the plunger 40 is translatable within the cavity 24 and the chamber 70 along the central longitudinal axis 30. Further, the sensor system 112 may also include a fluid 72 disposed within the chamber 70. The fluid 72 may be transitionable between a liquid phase (denoted generally at 74 in FIGS. 3C and 3D) and a solid phase (denoted generally at 76 in FIGS. 3A and 3B). That is, the fluid 72 may change viscosity as ambient temperature external to the housing 22 changes. In one example, the fluid 72 may be water, and may be present in the chamber 70 in the liquid phase 74 during the second condition 50 in which the housing 22 is substantially free from the coating of debris 14 (FIGS. 3A and 3B). Conversely, the fluid 72 may be present in the chamber 70 as ice in the solid phase 76 during the first condition 48 in which the coating of debris 14 is disposed on the housing 22.

As such, referring to FIGS. 3A and 3B, the plunger 40 may not retract into the cavity 24 when the fluid 72 has the solid phase 76. In contrast, referring to FIGS. 3C and 3D, the plunger 40 may be retractable into the cavity 24 when the fluid 72 has the liquid phase 74. Stated differently, when ambient conditions external to the housing 22 are sufficient to transition the fluid 72 from the liquid phase 74 to the solid phase 76, i.e., to freeze the fluid 72, the controller 64 may interpret the first stress 46 (FIG. 3B) and/or the first electrical resistance 60 (FIG. 3B) and alert a vehicle operator to the first condition 48 wherein the coating of debris 14 is disposed on the housing 22. Conversely, when ambient conditions external to the housing 22 are sufficient to transition the fluid 72 from the solid phase 76 to the liquid phase 74, i.e., to melt the fluid 72, the controller 64 may interpret the second stress 52 (FIG. 3D) and/or the second electrical resistance 62 (FIG. 3D) and alert a vehicle operator to the second condition 50 wherein the housing 22 is substantially free from the coating of debris 14.

Figure 4A:
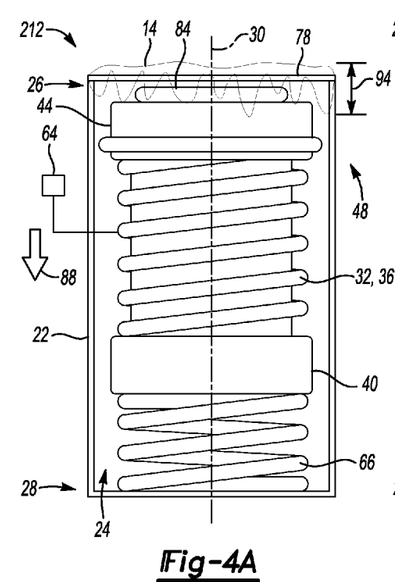
FIG. 4A is a schematic illustration of a side view of a further embodiment of the sensor system of FIG. 1 during the first condition before actuation of the actuator formed from the shape memory alloy, wherein the sensor system includes a flexible membrane.
Figure 4B:
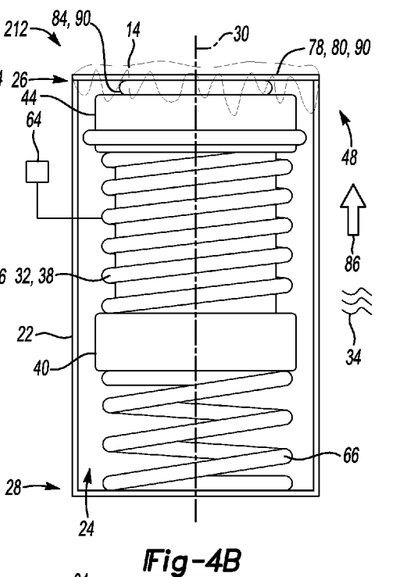
FIG. 4B is a schematic illustration of a side view of the sensor system of FIG. 4A during the first condition after actuation of the actuator.
Figure 4C:
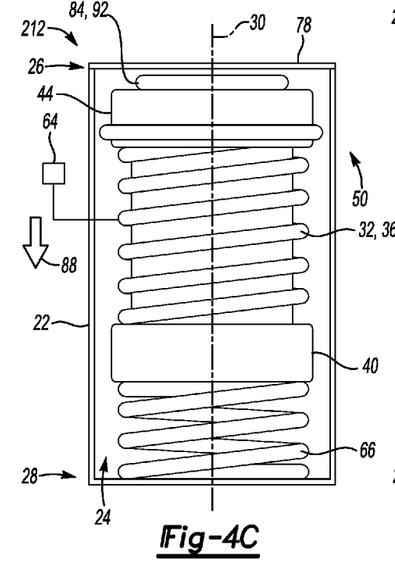
FIG. 4C is a schematic illustration of a side view of the sensor system of FIG. 4A during the second condition before actuation of the actuator.
Figure 4D:
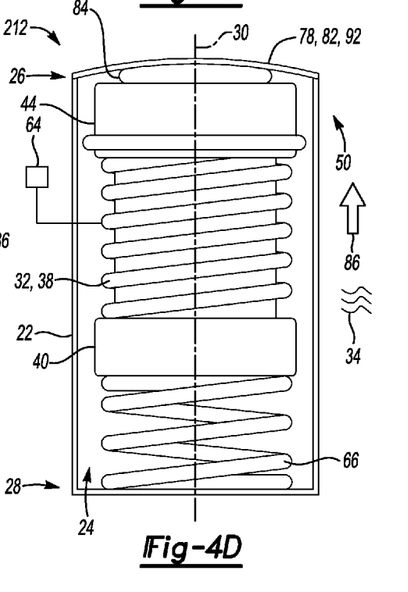
FIG. 4D is a schematic illustration of a side view of the sensor system of FIG. 4C during the second condition after actuation of the actuator.

Referring now to FIGS. 4A-4D, in a further embodiment, the sensor system 212 may include a flexible membrane 78 disposed on the proximal end 26. The flexible membrane 78 may have a first shape 80 (FIG. 4B) during the first condition 48 (FIGS. 4A and 4B) and a second shape 82 (FIG. 4D) that is different from the first shape 80 during the second condition 50 (FIGS. 4C and 4D). That is, as set forth in more detail below, the flexible membrane 78 may flex comparatively more during the second condition 50 in which the housing 22 is substantially free from the coating of debris 14, than during the first condition 48 in which the coating of debris 14 is disposed on the housing 22. Stated differently, the coating of debris 14 may minimize or prevent deformation of the flexible membrane 78. Conversely, the flexible membrane 78 may more readily deform, e.g., bulge or flex outward from the proximal end 26, when the housing 22 is substantially free from the coating of debris 14.

With continued reference to FIGS. 4B and 4D, the plunger 40 may be abuttable with the flexible membrane 78. More specifically, as shown in FIG. 4D and set forth in more detail below, the plunger 40 may abut and deform the flexible membrane 78 during the second condition 50 so that the flexible membrane 78 protrudes away from the cavity 24 and the housing 22 at the proximal end 26. However, as best shown in FIG. 4B, the plunger 40 may abut and may not deform the flexible membrane 78 during the first condition 48 so that the flexible membrane 78 does not protrude away from the cavity 24 and the housing 22 at the proximal end 26.

Further, as shown in FIGS. 4A-4D, to effect retraction and allow for resetting of the sensor system 212, the sensor system 212 may include the resilient member 66 attached to the distal end 28. The resilient member 66 may translate the plunger 40 away from the flexible membrane 78, i.e., may retract the plunger 40 away from the proximal end 26 into the cavity 24. For example, the resilient member 66 may be configured as a coil spring and may be attached to the actuator 32.

Therefore, in operation during the second condition 50 as described with reference to FIG. 4D, the actuator 32 may translate the plunger 40 within the cavity 24 towards the proximal end 26 in the direction of arrow 86 as the shape memory alloy transitions from the first temperature-dependent state 36 (FIG. 4C) to the second temperature-dependent state 38 (FIG. 4D) so that the plunger 40 abuts the flexible membrane 78, and the flexible membrane 78 protrudes from the cavity 24 and the housing 22 at the proximal end 26. That is, as the shape memory alloy transitions from the first temperature-dependent state 36 (FIG. 4C) to the second temperature-dependent state 38 (FIG. 4D), the actuator 32 may contract and shorten in length to thereby pull the plunger towards the flexible membrane 78. As the plunger 40 abuts the flexible membrane 78 and continues to translate away from the distal end 28 of the housing 22, the plunger 40 may push the flexible membrane 78 away from the distal end 28 so that the flexible membrane 78 is no longer flush with the proximal end 26 but rather protrudes from the housing 22. As set forth above, the flexible membrane 78 may have the second shape 82, and may deform upon contact with the plunger 40 since deformation or flex of the flexible membrane 78 is not limited since the coating of debris 14 is not disposed on the flexible membrane 78.

Conversely, in operation during the first condition 48 as described with reference to FIGS. 4A and 4B, the actuator 32 may translate the plunger 40 within the cavity 24 towards the proximal end 26 in the direction of arrow 86 as the shape memory alloy transitions from the first temperature-dependent state 36 (FIG. 4A) to the second temperature-dependent state 38 (FIG. 4B) so that the plunger 40 abuts the flexible membrane 78, and the flexible membrane 78 does not protrude from the housing 22 at the proximal end 26. That is, as the shape memory alloy transitions from the first temperature-dependent state 36 (FIG. 4A) to the second temperature-dependent state 38 (FIG. 4B), the actuator 32 may contract and shorten in length to thereby pull the plunger towards the flexible membrane 78. However, during the first condition 48, as the plunger 40 abuts the flexible membrane 78 and continues to translate away from the distal end 28 of the housing 22, the flexible membrane 78 may remain flush with the proximal end 26 and may not protrude from the housing 22.

Stated differently, with continued reference to FIGS. 4A and 4B, since the housing 22 and proximal end 26 are substantially covered with the coating of debris 14 during the first condition 48, the flexible membrane 78 may have the first shape 80 and may not flex outward from the cavity 24 and the housing 22 at the proximal end 26. Conversely, referring to FIGS. 4C and 4D, since the housing 22 and proximal end 26 are substantially free from the coating of debris 14 during the second condition 50, the flexible membrane 78 may have the second shape 82 and may flexibly deform, e.g., extend from the cavity 24 and the housing 22 at the proximal end 26, as the plunger 40 pushes against the flexible membrane 78. As such, the controller 64 may be configured to monitor and/or measure the flexibility of the flexible membrane 78 and alert a vehicle operator when the flexible membrane 78 has the first shape 80, i.e., when the sensor system 212 detects the first condition 48.

Referring again to FIGS. 4A-4D, to reset the sensor system 212, the resilient member 66 may retract the plunger 40 into the cavity 24 towards the distal end 28 after the shape memory alloy transitions from the second temperature-dependent state 38 (FIG. 4D) to the first temperature-dependent state 36 (FIG. 4C) so that the plunger 40 does not abut the flexible membrane 78, and the flexible membrane 78 does not protrude from the housing 22 at the proximal end 26. That is, during both the first condition 48 (FIGS. 4A and 4B) and the second condition 50 (FIGS. 4C and 4D), the actuator 32 may decrease in stiffness as the shape memory alloy transitions from the second temperature-dependent state 38 to the first temperature-dependent state 36, and the resilient member 66 may stretch the actuator 32 to thereby pull the plunger 40 in the direction of arrow 88 towards the distal end 28 of the housing 22. As such, the plunger 40 may no longer abut the flexible membrane 78 so that the flexible membrane 78 does not protrude from the housing 22 at the proximal end 26. That is, the resilient member 66 may reset the plunger 40 so that the flexible membrane 78 is substantially flush with the proximal end 26.

The flexible membrane 78 may be formed from any flexible material, such as, but not limited to, polymers and metals. In one non-limiting example, the flexible membrane 78 may be a piezoelectric polymer film and may exhibit a first voltage 90 (FIG. 4B) during the first condition 48 and a second voltage 92 (FIG. 4D) that is less than the first voltage 90 during the second condition 50. That is, as the piezoelectric polymer film flexes upon contact with the plunger 40 as described above, the first voltage 90 may be monitored to indicate the presence and/or a thickness 94 (FIG. 4A) of the coating of debris 14. For example, the second voltage 92 may increase to the first voltage 90 as the piezoelectric polymer film compresses. Alternatively or additionally, a strength of the thermal activation signal 34 (FIGS. 4B and 4D) may be compared to a time interval in which the shape memory alloy transitions from the first temperature-dependent state 36 (FIG. 4B) to the second temperature-dependent state 38 (FIG. 4D), i.e., an actuation time, to determine whether the sensor system 212 is operating within the first condition 48.

With continued reference to FIGS. 4A-4D, the sensor system 212 may further include a piezoelectric element 84 disposed on the plunger 40 at the indicator end 44. The piezoelectric element 84 may be formed from a piezoelectric material, such as, for example, a piezoceramic, and may be configured as one or more disks or wafers disposed on the indicator end 44 of the plunger 40. The piezoelectric element 84 may exhibit the first voltage 90 (FIG. 4B) during the first condition 48 and the second voltage 92 (FIG. 4C) that is different from the first voltage 90 during the second condition 50. That is, as the piezoelectric element 84 compresses, even slightly, upon movement in the direction of either of arrows 86, 88, and/or upon contact with the flexible member 78 as described above, the first voltage 90 may be monitored to indicate the presence of the coating of debris 14. For example, the second voltage 92 may increase to the first voltage 90 as the piezoelectric element 84 compresses. That is, the piezoelectric element 84 may exhibit a voltage 90, 92 that is directly proportional to an amount of loading of the piezoelectric material 84. Stated differently, the piezoelectric material 84 may generate a voltage 90, 92 that is proportional to a load or force of the plunger 40 pushing against the flexible membrane 78. As such, when the coating of debris 14 is disposed on the flexible membrane 78 and the flexible membrane 78 is not free to flex or translate away from the cavity 24 and the housing 22 at the proximal end 26, the voltage 90, 92 may indicate the presence and/or thickness 94 (FIG. 4A) of the coating of debris 14.

Referring now to FIGS. 5A-5F, the sensor system 212 may further include a cleaning apparatus 96, 196, 296, 396, 496, 596 adjoining the flexible membrane 78. The cleaning apparatus 96, 196, 296, 396, 496, 596 may be configured for vibrating the flexible membrane 78 to thereby displace the coating of debris 14 (FIG. 4A) from the housing 22 (FIG. 4A). For example, when the first condition 48 (FIGS. 4A and 4B) is detected by the sensor system 212 as set forth above, the cleaning apparatus 96 may vibrate the flexible membrane 78 such that the coating of debris 14 loosens and falls off the flexible membrane 78 at the housing 22.

Figure 5A:
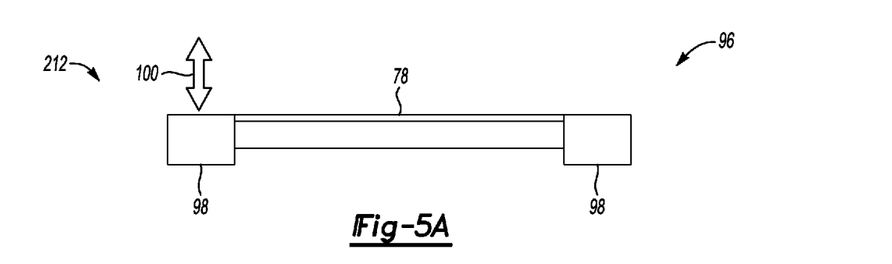
FIG. 5A is a schematic illustration of a side view of a portion of the flexible membrane of FIGS. 4A-4D disposed adjacent to a cleaning apparatus.

In one non-limiting embodiment shown in FIG. 5A, the cleaning apparatus 96 may include one or more ultrasonic transducers 98 disposed adjacent and in contact with the flexible membrane 78. That is, the one or more ultrasonic transducers 98 may adjoin the flexible membrane 78, but may not impede a line of sight through the flexible membrane 78. Upon detection of the first condition 48 (FIG. 4A), the one or more ultrasonic transducers 98 may vibrate, e.g., in the direction of alternating arrows 100, to loosen and displace the coating of debris 14 (FIG. 4B) from the flexible membrane 78 and housing 22 (FIG. 4A).

Figure 5B:
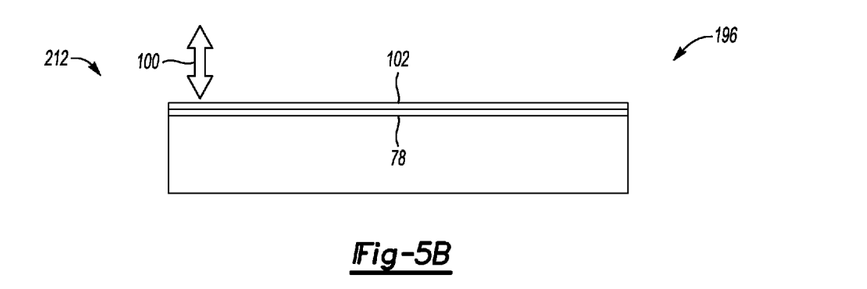
FIG. 5B is a schematic illustration of a side view of a portion of the flexible membrane of FIGS. 4A-4D disposed adjacent to a second embodiment of the cleaning apparatus of FIG. 5A.

Referring now to FIG. 5B, in another non-limiting embodiment, the cleaning apparatus 196 may include a second film 102 formed from a transparent piezoelectric polymer and disposed on the flexible membrane 78. That is, the second film 102 may cover the flexible membrane 78 but may be transparent so as not to impede a line of sight through the flexible membrane 78. Upon detection of the first condition 48 (FIG. 4A), the second film 102 may vibrate, e.g., in the direction of alternating arrows 100, to loosen and displace the coating of debris 14 (FIG. 4A) from the flexible membrane 78 and housing 22 (FIG. 4A).

Figure 5C:
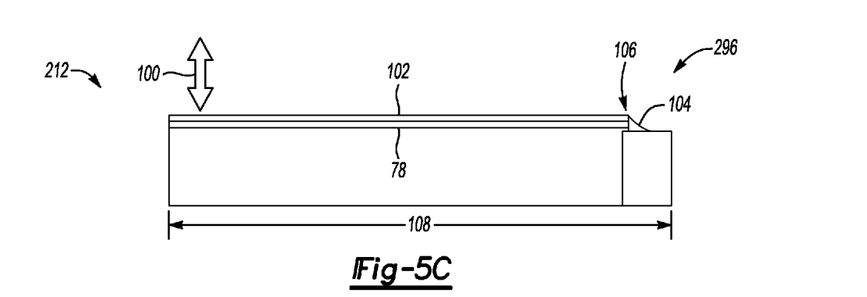
FIG. 5C is a schematic illustration of a side view of a portion of the flexible membrane of FIGS. 4A-4D disposed adjacent to a third embodiment of the cleaning apparatus of FIG. 5A.

In a further non-limiting embodiment described with reference to FIG. 5C, the cleaning apparatus 296 may include a finger 104 disposed in intermittent contact with the second film 102 to selectively lift the second film 102 at one end 106 to produce a ripple or wave (not shown) in the second film 102. Upon detection of the first condition 48 (FIG. 4A), the ripple or wave may translate across an entire length 108 of the second film 102, and the second film 102 may vibrate at a comparatively high amplitude, e.g., in the direction of alternating arrows 100, to loosen and displace the coating of debris 14 (FIG. 4A) from the flexible membrane 78 and housing 22 (FIG. 4A).

Figure 5D:
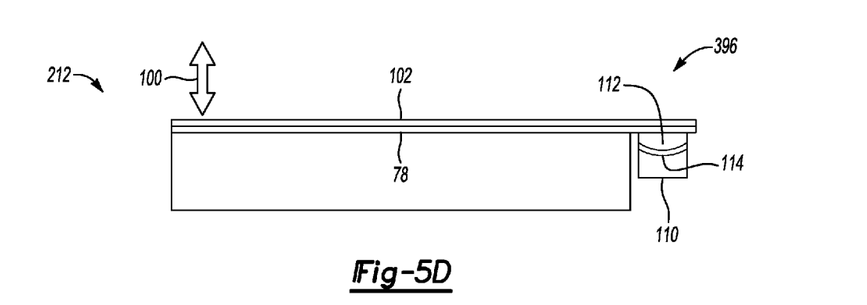
FIG. 5D is a schematic illustration of a side view of a portion of the flexible membrane of FIGS. 4A-4D disposed adjacent to a fourth embodiment of the cleaning apparatus of FIG. 5A.

In yet another non-limiting embodiment described with reference to FIG. 5D, the cleaning apparatus 396 may include a speaker 110 defining an opening 112 therein and disposed adjacent and in contact with the second film 102. Further, the cleaning apparatus 396 may include a third film 114 formed from the transparent piezoelectric polymer and disposed within the opening 112. Upon detection of the first condition 48 (FIG. 4A), the third film 114 may vibrate within the opening 112 to thereby produce a sound pressure wave (not shown) within the opening 112. As the sound pressure wave transmits to the second film 102, the second film 102 may vibrate, e.g., in the direction of alternating arrows 100, to loosen and displace the coating of debris 14 (FIG. 4A) from the flexible membrane 78 and housing 22 (FIG. 4A).

Figure 5E:
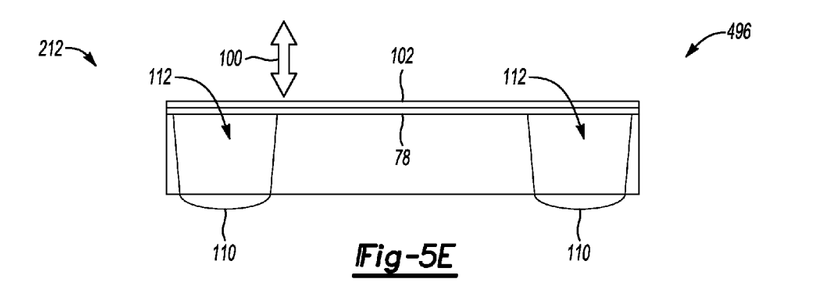
FIG. 5E is a schematic illustration of a side view of a portion of the flexible membrane of FIGS. 4A-4D disposed adjacent to a fifth embodiment of the cleaning apparatus of FIG. 5A.

Referring to FIG. 5E, in an additional non-limiting embodiment, the cleaning apparatus 496 may include a plurality of speakers 110 each defining an opening 112 therein, and the second film 102 may cover each respective opening 112. Upon detection of the first condition 48 (FIG. 4A), each speaker 110 may produce a sound pressure wave (not shown) within each opening 112. As the sound pressure wave transmits to the second film 102, the second film 102 may vibrate, e.g., in the direction of alternating arrows 100, to loosen and displace the coating of debris 14 (FIG. 4A) from the flexible membrane 78 and housing 22 (FIG. 4A).

Figure 5F:
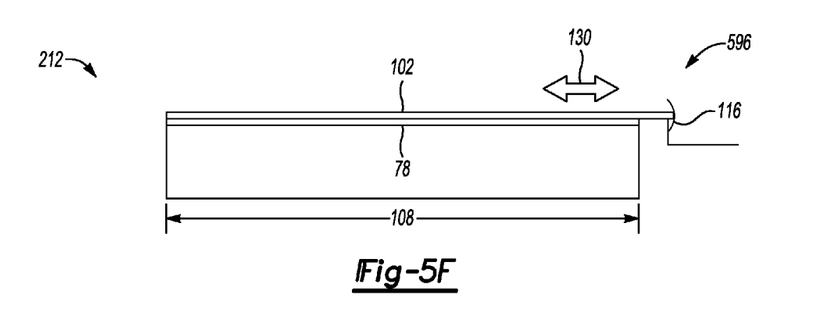
FIG. 5F is a schematic illustration of a side view of a portion of the flexible membrane of FIGS. 4A-4D disposed adjacent to a sixth embodiment of the cleaning apparatus of FIG. 5A.

Referring now to FIG. 5F, in another non-limiting embodiment, the cleaning apparatus 596 may include a driving member 116 configured to translate or shake the second film 102 across the length 108 of the proximal end 26 (FIG. 4A). Therefore, upon detection of the first condition 48 (FIG. 4A), the driving member 116 may alternately push and pull against the second film 102, e.g., in the direction of arrows 130, so that the second film 102 vibrates to loosen and displace the coating of debris 14 (FIG. 4A) from the flexible membrane 78 and housing 22 (FIG. 4A).

Figure 6:
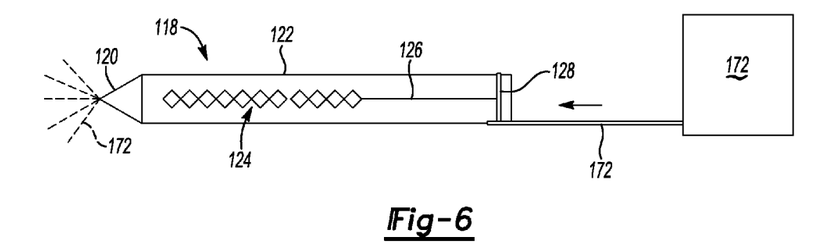
FIG. 6 is a schematic illustration of a side view of a sprayer configured for cleaning the sensor system of FIGS. 1-5D.

Referring now to FIG. 6, alternatively or additionally, the sensor system 212 (FIGS. 4A-4D) may further include a sprayer 118 configured for cleaning the flexible membrane 78 (FIG. 4A). That is, a nozzle 120 of the sprayer 118 may be directed to spray a fluid 172, such as a solvent or water, onto the flexible membrane 78. In particular, the sprayer 118 may include a canister 122 defining a void 124 therein, a wire 126, and the fluid 172. The wire 126 may be attached to the canister 122 within the void 124 and may be formed from the shape memory alloy. Further, the fluid 172 may be disposed within the void 124 and may be warmable as the shape memory alloy transitions from the first temperature-dependent state 36 (FIG. 4A) to the second temperature-dependent state 38 (FIG. 4B). Upon detection of the first condition 48 (FIGS. 4A and 4B), the shape memory alloy may transition from the first temperature-dependent state 36 to the second temperature-dependent state 38 to both warm the fluid 172 and actuate the sprayer 118. That is, the wire 126 may actuate a valve (shown generally at 128) so that the sprayer 118 discharges the fluid 172 from the void 124 through the nozzle 120 to remove the coating of debris 14 (FIG. 4A) from the proximal end 26 (FIG. 4A), and thereby clean the flexible membrane 78.

Therefore, the cleaning apparatus 96, 196, 296, 396, 496, 596 and/or sprayer 118 may clean and protect the sensor system 212 (FIGS. 4A-4D). In particular, the cleaning apparatus 96, 196, 296, 396, 496, 596 and/or sprayer 118 may remove the coating of debris 14 (FIG. 4A) from a line of sight of the sensor system 212 without manual intervention by an operator of the vehicle 10 (FIG. 1).

For any of the embodiments described herein, the sensor system 12, 112, 212, cleaning apparatus 96, 196, 296, 396, 496, 596, and/or sprayer 118 may be combined with other cleaning and/or protection systems (not shown). By way of non-limiting examples, the flexible membrane 78 and/or plunger 40 may be cleaned and/or protected by any of the following methods. The flexible membrane 78 and/or plunger 40 may be heated to melt the coating of debris 14. The coating of debris 14 may be wiped or cleared from the flexible membrane 78 and/or plunger 40 by one or more wipers or blades (not shown). The sensor system 12, 112, 212 may include an automatic or selectively-activated cover (not shown) configured to cover the flexible membrane 78 and/or plunger 40 when not in use. Further, air jets (not shown) may transfer air under pressure to the flexible membrane 78 and/or plunger 40 to thereby disrupt the coating of debris 14. Likewise, ambient air or heated air from an exhaust of the vehicle 10 may be directed to the flexible membrane 78 and/or plunger 40 through vanes, vents, and/or flaps. Further, the flexible membrane 78 and/or plunger 40 may be substantially coated with a non-stick coating, such as polytetrafluoroethylene.

In addition, for any of the embodiments described herein, the shape memory alloy may be actuated by exposing the shape memory alloy to the thermal activation signal 34. Further, for vehicle applications, actuation of the shape memory alloy may be automatically triggered by sensors (not shown) configured to detect temperature, water, dust, and the like. Alternatively or additionally, the shape memory alloy may be automatically triggered upon vehicle start-up, or, for example, when the vehicle 10 shifts into reverse, activates a turn signal, activates landing gear, etc. Furthermore, the shape memory alloy may be triggered solely upon operator input, i.e., on demand as determined by an operator of the vehicle 10.

Therefore, the aforementioned sensor systems 12, 112, 212 and vehicle 10 provide excellent debris detection. That is, the sensor systems 12, 112, 212 may detect not only the presence of the coating of debris 14, but a thickness 94 (FIG. 4A) of the coating of debris 14. Further, the sensor systems 12, 112, 212 may detect the coating of debris 14 without reliance on measurement of ambient temperature. Such sensor systems 12, 112, 212 may therefore warn a vehicle operator of environmental conditions which may detract from optimal functioning of the vehicle 10 or vehicle components. As such, the sensor systems 12, 112, 212 improve convenience and eliminate manual cleaning of the sensor systems 12, 112, 212 in order to clear a line of sight of the sensor systems 12, 112, 212. Further, the sensor systems 12, 112, 212 are economical and easily integrated into the vehicle 10.

While the best modes for carrying out the present invention have been described in detail, those familiar with the art to which this invention relates will recognize various alternative designs and embodiments for practicing the invention within the scope of the appended claims.

The invention claimed is:

1. A sensor system for a vehicle, the sensor system comprising:
   a housing defining a cavity therein;
   an actuator attached to the housing within the cavity and formed from a shape memory alloy transitionable in response to a thermal activation signal between a first temperature-dependent state and a second temperature-dependent state;
   a plunger attached to the actuator and translatable within the cavity;
   wherein the plunger is not translatable within the cavity during a first condition in which a coating of debris is disposed on the housing as the shape memory alloy transitions between the first temperature-dependent state and the second temperature-dependent state to thereby define a first stress on the actuator;
   wherein the plunger is translatable within the cavity during a second condition in which the housing is substantially free from the coating of debris as the shape memory alloy transitions between the first temperature-dependent state and the second temperature-dependent state to thereby define a second stress on the actuator that is less than the first stress;
   wherein the shape memory alloy transitions from the first temperature-dependent state to the second temperature-dependent state at a first transformation temperature during the first condition; and
   wherein the shape memory alloy transitions from the first temperature-dependent state to the second temperature-dependent state at a second transformation temperature that is less than the first transformation temperature during the second condition; and
   a resilient member configured for translating the plunger within the cavity after the shape memory alloy transitions from the second temperature-dependent state to the first temperature-dependent state.

2. The sensor system of claim 1, wherein the housing has:
   a proximal end spaced apart from the actuator;
   a distal end spaced apart from the proximal end; and
   a central longitudinal axis extending from the proximal end to the distal end along which the plunger translates within the cavity.

3. The sensor system of claim 2, wherein the plunger protrudes from the cavity at the proximal end.

4. The sensor system of claim 3, wherein the plunger has an attachment end attached to the actuator and spaced apart from the proximal end, and an indicator end spaced apart from the attachment end, and further wherein the attachment end translates along the central longitudinal axis from a first position on the central longitudinal axis to a second position on the central longitudinal axis during the second condition.

5. The sensor system of claim 4, wherein the resilient member translates the plunger from the second position to the first position so that the plunger protrudes from the housing at the proximal end after the shape memory alloy transitions from the second temperature-dependent state to the first temperature-dependent state.

6. The sensor system of claim 3, wherein the shape memory alloy exhibits a first electrical resistance during the first condition, and exhibits a second electrical resistance during the second condition that is less than the first electrical resistance.

7. The sensor system of claim 6, further including a controller connected to the actuator and configured for indicating the first electrical resistance.

8. The sensor system of claim 3, further including:
   a cap attached to the proximal end and defining a chamber therein that is disposed in communication with the cavity so that the plunger is translatable within the cavity and the chamber along the central longitudinal axis; and
   a fluid disposed within the chamber and transitionable between a liquid phase and a solid phase.

9. The sensor system of claim 8, wherein the plunger is not retractable into the cavity when the fluid has the solid phase.

10. The sensor system of claim 9, wherein the plunger is retractable into the cavity when the fluid has the liquid phase.

11. The sensor system of claim 3, further including a flexible membrane disposed on the proximal end, wherein the plunger abuts and does not deform the flexible membrane so that the flexible membrane does not protrude away from the cavity and the housing at the proximal end during the first condition.

12. The sensor system of claim 11, wherein the plunger abuts and deforms the flexible membrane so that the flexible membrane protrudes away from the cavity and the housing at the proximal end during the second condition.

13. The sensor system of claim 12, wherein the plunger has an attachment end attached to the actuator and spaced apart from the proximal end, and an indicator end spaced apart from the attachment end, and further including a piezoelectric element disposed on the plunger at the indicator end, wherein the piezoelectric element exhibits a first voltage during the first condition and a second voltage that is different from the first voltage during the second condition.

14. The sensor system of claim 11, wherein the resilient member is attached to the distal end and translates the plunger away from the flexible membrane.

15. The sensor system of claim 11, further including a cleaning apparatus adjoining the flexible membrane and configured for vibrating the flexible membrane to thereby displace the coating of debris from the housing.

16. A sensor system for a vehicle, the sensor system comprising:
a housing defining a cavity therein and having a proximal end and a distal end spaced apart from the proximal end;
an actuator attached to the housing within the cavity at the distal end and formed from a shape memory alloy transitionable in response to a thermal activation signal between a first temperature-dependent state and a second temperature-dependent state;
a flexible membrane disposed on the proximal end;
a plunger attached to the actuator, translatable within the cavity, and abuttable with the flexible membrane;
wherein the plunger is not translatable within the cavity during a first condition in which a coating of debris is disposed on the flexible membrane as the shape memory alloy transitions between the first-temperature dependent state and the second temperature-dependent state to thereby define a first stress on the actuator;
wherein the plunger is translatable within the cavity during a second condition in which the flexible membrane is substantially free from the coating of debris as the shape memory alloy transitions between the first temperature-dependent state and the second temperature-dependent state to thereby define a second stress on the actuator that is less than the first stress;
wherein the shape memory alloy transitions from the first temperature-dependent state to the second temperature-dependent state at a first transformation temperature during the first condition;
wherein the shape memory alloy transitions from the first temperature-dependent state to the second temperature-dependent state at a second transformation temperature that is less than the first transformation temperature during the second condition; and
a resilient member configured for translating the plunger within the cavity after the shape memory alloy transitions from the second temperature-dependent state to the first temperature-dependent state;
wherein the resilient member retracts the plunger into the cavity towards the distal end after the shape memory alloy transitions from the second temperature-dependent state to the first temperature-dependent state so that the plunger does not abut the flexible membrane and the flexible membrane does not protrude from the housing at the proximal end;
wherein the actuator translates the plunger within the cavity towards the proximal end during the first condition as the shape memory alloy transitions from the first temperature-dependent state to the second temperature-dependent state so that the plunger abuts the flexible membrane and the flexible membrane does not protrude from the housing at the proximal end; and
wherein the actuator translates the plunger within the cavity towards the proximal end during the second condition as the shape memory alloy transitions from the first temperature-dependent state to the second temperature-dependent state so that the plunger abuts the flexible membrane and the flexible membrane protrudes from the cavity and the housing at the proximal end.

17. The sensor system of claim 16, wherein the flexible membrane is a piezoelectric polymer film and exhibits a first voltage during the first condition and a second voltage that is less than the first voltage during the second condition.

18. The sensor system of claim 16, further including a sprayer configured for cleaning the flexible membrane, wherein the sprayer includes:
a canister defining a void therein;
a wire attached to the canister within the void and formed from the shape memory alloy; and
a fluid disposed within the void and warmable as the shape memory alloy transitions from the first temperature-dependent state to the second temperature-dependent state; and
further wherein the sprayer discharges the fluid from the void to remove the coating of debris from the proximal end and thereby clean the flexible membrane.

19. A vehicle comprising:
a body defining an aperture therein; and
a sensor system disposed within the aperture and including:
a housing defining a cavity therein;
an actuator attached to the housing within the cavity and formed from a shape memory alloy transitionable in response to a thermal activation signal between a first temperature-dependent state and a second temperature-dependent state;
a plunger attached to the actuator and translatable within the cavity;
wherein the plunger is not translatable within the cavity during a first condition in which a coating of debris is disposed on the housing as the shape memory alloy transitions between the first temperature-dependent state and the second temperature-dependent state to thereby define a first stress on the actuator;
wherein the plunger is translatable within the cavity during a second condition in which the housing is substantially free from the coating of debris as the shape memory alloy transitions between the first temperature-dependent state and the second temperature-dependent state to thereby define a second stress on the actuator that is less than the first stress;
wherein the shape memory alloy transitions from the first temperature-dependent state to the second temperature-dependent state at a first transformation temperature during the first condition; and
wherein the shape memory alloy transitions from the first temperature-dependent state to the second temperature-dependent state at a second transformation temperature that is less than the first transformation temperature during the second condition; and
a resilient member configured for translating the plunger within the cavity after the shape memory alloy transitions from the second temperature-dependent state to the first temperature-dependent state.

* * * * *